United States Patent [19]

Mulqueen et al.

[11] Patent Number: 4,581,373

[45] Date of Patent: Apr. 8, 1986

[54] DERIVATIVES OF BIOLOGICALLY ACTIVE SUBSTITUTED TIN COMPOUNDS, EMULSIFIABLE CONCENTRATES OF SAID DERIVATIVES AND METHOD OF CONTROLLING PLANT INFESTATIONS

[75] Inventors: Patrick J. Mulqueen; Robert Dutton, both of King's Lynn, United Kingdom

[73] Assignee: The Dow Chemical Company, Midland, Mich.

[21] Appl. No.: 459,161

[22] Filed: Jan. 19, 1983

[51] Int. Cl.$^4$ .................... A01N 55/04; A61K 31/32; C07F 7/28

[52] U.S. Cl. ........................................ 514/493; 71/86; 71/97; 556/24; 556/88

[58] Field of Search ...................... 260/429.7; 424/288; 71/86, 97; 551/24, 88; 514/493

[56] References Cited

U.S. PATENT DOCUMENTS

| | | | |
|---|---|---|---|
| 2,786,812 | 3/1957 | McDermott | 260/429.7 |
| 3,140,977 | 7/1964 | Duyfjes et al. | 260/429.7 X |
| 3,201,432 | 8/1965 | Leebrick | 260/429.7 |
| 3,264,177 | 8/1966 | Kenaga | 424/288 |
| 3,268,395 | 8/1966 | Taylor | 424/288 |
| 3,358,006 | 12/1967 | Walsh et al. | 260/429.7 |
| 3,395,228 | 7/1968 | Dacus | 424/288 |
| 3,538,088 | 11/1970 | Hartmann | 260/429.7 X |
| 3,634,479 | 1/1972 | Ridenour et al. | 260/429.7 |
| 3,703,588 | 11/1972 | Saito et al. | 260/429.7 |
| 3,791,811 | 2/1974 | French et al. | 424/288 X |
| 3,947,481 | 3/1976 | Baker | 260/429.7 |
| 3,992,425 | 11/1976 | Baker | 260/429.7 |
| 4,010,276 | 3/1977 | Gitlitz | 424/288 |
| 4,012,421 | 3/1977 | Baker | 260/429.7 |
| 4,071,545 | 1/1978 | Mihailovski | 260/429.7 |
| 4,209,452 | 6/1980 | Strunk et al. | 424/288 |

OTHER PUBLICATIONS

Chemical Abstracts, 93, 71881u, 71884x (1980).
Chemical Abstracts, 96, 153121x (1982).
Chemical Abstracts, 85, 178215s (1976).
Lefferts et al, Inorg. Chem., 19(6) 1662–1670, abstract (1980).
Sawyer, Organotin Compounds, Marcel Dekker, N.Y., pp. 276 to 278, 404 & 475 to 477 (1971).

*Primary Examiner*—Helen M. S. Sneed
*Attorney, Agent, or Firm*—Merlin B. Davey

[57] ABSTRACT

A derivative of a biologically active substituted tin compound with a lipophilic strong acid containing sulphur or phosphorus, or a salt thereof. These derivatives are readily soluble in organic liquids and are thus readily formulated as emulsifiable concentrates.

17 Claims, No Drawings

DERIVATIVES OF BIOLOGICALLY ACTIVE SUBSTITUTED TIN COMPOUNDS, EMULSIFIABLE CONCENTRATES OF SAID DERIVATIVES AND METHOD OF CONTROLLING PLANT INFESTATIONS

The present invention relates to derivatives of biologically active substituted tin compounds, emulsifiable concentrates containing the derivatives and to methods for controlling plant infestations using the substituted tin derivatives.

Tricyclohexyltin hydroxide (commonly referred to as cyhexatin) is an acaricide effective by contact against the motile stages of a wide range of phytophagus mites, such as *Tetranychus urticae*. It is generally essentially insoluble in water and most common organic solvents suitable for use in agrochemical formulations e.g., aromatic hydrocarbons such as xylene. For this reason, cyhexatin has been prepared in the form of particulate preparations, such as a wettable powder.

More recently, the ability to reduce the particle size in a wet-milling process has lead to the development of a suspension of cyhexatin in water which is used as an aqueous flowable formulation. It is, however, a complicated production process to balance the optimum activity with the desired lack of phytotoxicity of the cyhexatin to the crops, e.g., hops, citrus and deciduous fruits in formulations containing particulare cyhexatin.

A considerable amount of research has been conducted in an effort to produce solutions of cyhexatin in an organic solvent (containing an emulsifier) which solutions can readily be dispersed in water. These concentrated solutions are generally referred to as "emulsifiable concentrates". Unfortunately, heretofore, emulsifiable concentrates of cyhexatin have been generally deficient in their pesticidal activity, or possessed increased phytotoxicity. Therefore emulsifiable concentrations of cyhexatin have not been commercially available.

Triphenyltin hydroxide (commonly referred to as fentin hydroxide) is a non-systemic fungicide effective for the control of early and late blights of potato, leaf spot on sugar beet and similar fungicidal diseases. It is also generally essentially insoluble in water. Although soluble to a limited degree in various common organic liquids, the fentin hydroxide is often phytotoxic in emulsifiable concentrate formulations. For this reason, when employed for the control of plant fungi against which fentin hydroxide is active, the formulations of fentin hydroxide have been prepared as a wettable powder or as a concentration, aqueous suspension. These however show only a short persistence of activity under the normal climate conditions of use, since particulate materials are usually readily washed off the plants.

Surprisingly, it has now been found that the lipophilic strong anionic derivatives of biologically active substituted tin compound are readily soluble in common, organic liquids, In one aspect, the present invention provides a derivative of a biologically active substituted tin compound with a lipophilic strong acid containing sulphur or phosphorus, or a salt thereof.

Due to their increased solubility in common organic solvents suitable for use in agricultural formulation, the derivatives are easily formulated as emulsifiable concentrates and, in another aspect, the present invention provides an emulsifiable concentrate of the substituted tin derivative in an organic liquid.

The derivatives of the present invention, when compared to the known formulations of cyhexatin and fentin hydroxide exhibit one or more of the following advantages:

(a) reduced phytotoxicity,
(b) increased efficacy,
(c) improved dilution characteristics,
(d) greater ease of application in aerial spraying,
(e) improved compatibility for formulation with other pesticides, or
(f) improved tank-mix compatibility with other pesticides.

The derivatives of the present invention are the lipophilic strong anionic derivatives of biologically active substituted tin compounds. By the term "lipophilic strong anion" as used herein, is meant the anion of an acid, or the salt thereof, containing a sulphur or phosphorus atom. Such strong acids have a PKa of 3 or below at 25° C., preferably below 2.5 at 25° C. Examples of such lipophilic strong anionic salts include sulphonates, particularly the aryl and aralkyl sulphonates; the sulphates particularly the alkyl and substituted alkyl sulphates; the phosphates; particularly the alkyl, aryl or aralkyl phosphates; the ether sulphates; the olefin sulphonates; the ether phosphates, the phosphonates, particularly the alkyl, aryl or aralkyl phosphonates; the sulphosuccinates; and the corresponding acids of such salts.

Due to the desirable balance between efficacy and phytotoxicity obtained, the most preferred or the lipophilic strong acids or their salts employed in the practice of the present invention are the alkylaryl sulphonic acids containing from 6 to 18 carbon atoms in the alkyl group, preferably the $C_6$-$C_{18}$ alkylbenzene sulphonic acids, most preferably dodecyl or tridecylbenzene sulphonic acid, and the alkali metal salts of the said acids.

The derivatives can be prepared in neat form by treating at room temperature the biologically active substituted tin compound with an approximately equivalent amount of the desired lipophilic strong acid or a suitable salt thereof in a relatively volatile organic liquid such as a lower alkane, e.g. hexane, or a substituted alkane, e.g. dichloromethane. Upon removal of the organic liquid, a technical grade product which can be formulated into conventional emulsifiable concentrates or flowable compositions is obtained.

The derivatives of the present invention may be formulated in various ways. For example, by properly selecting the diluent, the derivatives can be prepared as a solution, an aqueous dispersion, an aqueous emulsion, a dusting powder or a dispersible powder, an emulsifiable concentrate, a dispersible concentrate or an aerosol.

In a second aspect of the present invention, the derivatives are prepared as emulsifiable concentrates. In general emulsifiable concentrates are concentrated solutions of the biologically active substituted tin derivatives in an inert organic liquid. The term emulsifiable concentrate also includes concentrated emulsions containing the derivative, water and optionally an organic liquid for further dilution in water or organic liquids according to use requirements. Representative of inert organic liquids which can be employed in preparing the emulsifiable concentrates are the various aromatic liquids such as xylene, propylbenzene and mixed naphthalene fractions; mineral oils; substituted aromatic organic liquids such as dioctyl phthalate; dialkyl amides of various fatty carboxylic acids such as the dimethyl amide of caprylic acid; glycols and glycol derivatives such as the n-butyl ether, ethyl ether or methyl ether of diethylene glycol; the ether of triethylene glycol; the methyl ether of dipropylene glycol; the n-butyl ether of ethylene glycol; the ethyl, methyl or phenyl ether of ethylene glycol; or the methyl ether of propylene or tripropylene glycol; or mixtures thereof. The preferred organic liquids are the aromatic liquids, with xylene and propylbenzene fractions being most preferred.

The concentration of the derivative in the emulsifiable concentrate most advantageously employed will vary depending on the specific derivative and organic liquid employed and the desired end use application of the emulsifiable concentrate or the aqueous emulsion prepared therefrom. In general, the derivative is employed in an amount sufficient such that the desired concentration of the derivative is obtained upon subsequent dilution in water. In general, the emulsifiable concentrate will contain from 5 to 50, preferably from 20 to 40, weight percent of the substituted biologically active tin compound based on the total weight of the emulsifiable concentrate.

In addition to the organic liquid and the tin derivative, the emulsifiable concentrate will generally comprise at least of one a surfactant or emulsifier to ensure the ready dispersion of the concentrate upon its subsequent dilution in water. The surfactants suitably employed herein are those surface active agents which are compatible with the derivative and the organic liquid employed in preparing the emulsifiable concentrate and which permit the subsequent dispersion of the derivative as an emulsion in water. Emulsifiers which can be advantageously employed herein can be readily determined by those skilled in the art and include various nonionic, anionic, cationic or amphoteric emulsifiers, or a blend of two or more emulsifiers can be employed. Examples of nonionic emulsifiers useful in preparing the emulsifiable concentrates include the polyalkylene glycol ethers and condensation products of alkyl phenols, aliphatic alcohols, aliphatic amines or fatty acids with ethylene oxide, propylene oxide or mixtures of ethylene and propylene oxides such as the ethoxylated alkyl phenols, e.g., nonyl phenoxypoly (ethylene oxy) ethanol and ethoxylated aliphatic alcohols, e.g., alkyl poly (ethylene oxy) ethanol, and the carboxylic esters solubilized with the polyol or polyoxy ethylene. Cationic emulsifiers include quaternary ammonium compounds and fatty amines. Preferred emulsifiers for emulsifiable concentrates are nonionics and organosoluble anionics or blends thereof such as Tensiofix B7416 and B7453, with the most preferred being the alkoxylation derivatives of fatty amines, e.g., Ethomeen C-25.

The amounts of the tin derivatives most advantageously employed are dependent upon various factors including the specific derivative, surfactant and organic liquid employed in preparing the emulsifiable concentrate and the end use application. The surface is employed in an amount sufficient to ensure that the concentrate can be dispersed in water to form an emulsion or suspension having the desired stability. Such amounts will vary depending on the derivative and organic liquid employed in the emulsifiable concentrate and the desired end use application. In general, the emulsifiable concentrates will contain preferably from 20 to 40, weight percent of the substituted biologically active tin compound from 1.0 to 50 preferably from 10 to 35 weight percent of one or more emulsifiers, with a balance being the organic liquid or mixture of organic liquids.

In general, the anionic derivative of cyhexatin or fentin hydroxide is advantageously prepared directly in the form of an emulsifiable concentrate by admixing in the desired organic liquid, the cyhexatin or fentin hydroxide with the desired lipophilic strong acid without the need for heating to form a stable derivative. Although, in general, the emulsifiable concentrates are prepared as a dispersion of finely divided cyhexatin or fentin hydroxide derivatives in the liquid, by properly selecting the organic liquid and emulsifiers employed, the emulsifiable concentrates can be utilized as micellar solutions (solubilized formulations).

In conventional application the thus-prepared emulsifiable concentrates can be diluted in water to form an emulsion ready for use. Alternatively, by appropriate choice of solvents the emulsifiable concentrate can directly, or upon minimal dilution, be applied using ultra-low volume techniques (ULV). In addition, by the techniques described in G.B. patent application No. 2,022,401: S.A. patent application No. 79-2569: and EP application Nos. 0039144 and 0003251, the emulsifiable concentrates can be prepared for use as electrostatic or electrodynamic spray applications.

The emulsifiable concentrates of cyhexatin of the present invention can also be used as animal health care products in the treatment of animal and poultry ectoparasites such as ixodid ticks.

The present invention will be further described with reference to the following examples:

EXAMPLE 1

An emulsifiable concentrate of a cyhexatin derivative was prepared by slurrying cyhexatin (200 g) in xylene (400 g) at room temperature and adding dodecylbenzenesulphonic acid (176 g) to form a stable derivative. Following this neutralization the mixture was treated with a surfactant (Ethomeen C-25 [100 g]) and xylene added to volume (to 1 liter). The resultant solution concentrate contained 200 g/liter cyhexatin and was dilutable in water producing satisfactory emulsions for application to corps.

EXAMPLE 2

An emulsifiable concentrate of a cyhexatin derivative was prepared by slurrying cyhexatin (200 g) in dichloromethane (1 liter) at room temperature and adding dodecylbenzenesulphonic acid (176 g). The mixture after this neutralization was poured into water, the dichloromethane extract collected, dried and evaporated to give the dodecylbenzene sulphonic acid derivative. This derivative was a viscous oil which cystallised slowly on standing, m.p. 152°-6° C. Its structure was determined by elemental analysis and n.m.r. 36 g of this derivative (equivalent to 20 g cyhexatin) was formulated as an emulsifiable concentrate by mixing the following ingredients.

| | |
|---|---|
| Acid derivative (20 g cyhexatin) | 36 g |
| Tensiofix B 7416 | 3 g |
| Tensiofix B 7453 | 7 g |
| Xylene | to 100 |

EXAMPLE 3

An emulsifiable concentrate of a fentin hydroxide derivative was prepared by slurrying fentin hydroxide (200 g) in xylene (400 g) at room temperature and adding dodecylbenzenesulphonic acid (182 g). The mixture, after this neutralization was treated with a surfactant (Ethomeen C-25 [100 g]) and xylene added to volume (1 liter). The resultant emulsifiable concentrate contained 200 g/liter fentin hydroxide and was dilutable in water, producing satisfactory emulsions for application to crops.

EXAMPLE 4

In a similar manner to that described in Example 1 emulsifiable concentrates were produced by reaction of cyhexatin with the following acids:
(a) tridecylbenzenesulphonic acid.
(b) di-isooctyl-(1-sulphonic acid)butane-1,4-dicarboxylate.
(c) Emcol CS151 (a phosphate ester of an ethoxylated alkyl phenol with about 11 moles of ethylene oxide).
(d) Phospholan PNP-9 (a phosphate ester of an ethoxylated alkyl phenol with about 9 moles of ethylene oxide).
(e) Emcol CS131 (a phosphate ester of an ethoxylated alkyl phenol with about 6 moles of ethylene oxide).
(f) Emcol PS331 (a phosphate ester of an ethoxylated alcohol with about 6 moles of ethylene oxide).
(g) Emcol PS413 (a phosphate ester of an ethoxylated alcohol with about 2 moles of ethylene oxide).

EXAMPLE 5

Biological testing was carried out as follows using the cyhexatin e.c. from Example 1 as well as using as the control, an aqueous suspension concentrate formulation containing 600 g per liter cyhexatin (Plictran 600F) and as comparative formulations the lauric acid and oleic acid derivatives produced according to Example 4.

Slide Assay

Ten adult femal glasshouse red spider mites *Tetranychus urticae* (Koch) reared on pinto beans were fixed by their dorsal surfaces to 3"×1" glass microscope slides using double-sided tape. The experimental formulation was diluted in distilled water to the desired concentration and the solution was applied using a Potter Tower apparatus calibrated to produce a deposit of 600 liters per hectare.

The treated slides were allowed to dry under a fumehood and then incubated at 30° C. and 70-80 percent relative humidity. Mortality counts were made after 24 hours and the response expressed as a percentage.

The mortality data from the treatments were compared with that from the controls and asjusted using Abbot's formula. The percentage mortality: dose relationship is calculated and the final result is expressed as the parts per million necessary to give 90 percent kill.

Eradicant Assay

Active stage mites and eggs of the glasshouse red spider mite *Tetranychus urticae* (Koch) were reared onto pinto beans. For the experiments, individually potted pinto bean plants with two fully expanded true leaves were infected naturally with an inoculum of mites from the stock cultures 24 hours before treatment. Immediately prior to treatment, the dried remains of leaves from the inoculum were removed. Four plants were sprayed at each dose rate.

The formulations were diluted in distilled water to the desired concentration. The contaminated plants were treated on a turntable spray machine, each plant being rotated through two turns and at the same time sprayed from twin-jets so that the top and underside of the leaves are treated.

When dry, the treated plants are kept in a glasshouse at 20°-25° C., 70-80 percent relative humidity with a minimum 12 hour photoperiod.

The plants were assessed for activity using a low power binocular microscope after 48 hours and nine days using the following scores:
0=all mites alive as in controls
1=most mites alive; few dead
2=most mites dead; few alive
3=all mites dead The scores of the four replicates at each does rate are totalled to produce a score out of a maximum of 12. For comparative purposes, the Minimum Effective Concentration (MEC) is taken as a score of 10 out of 12.

The results of test were as follows:

|  | Eradicant (MEC) ppm | Phytotoxicity to Pinto Beans at 60 ppm | Slide $LC_{90}$ ppm |
|---|---|---|---|
| Experimental Formulation (Example 1) | 10-20 | 0 | 20-40 |
| Cyhexatin Control | 10-20 | 2.0 | 10-20 |
| Comparative Formulation A (Example 5 lauric acid) | 10-20 | 3.0 | 20-40 |
| Comparative Formulation B (Example 5 Oleic acid) | 10-20 | 3.0 | 20-40 |

The phytotoxicity was graded as follows:
0=none
1=slight
2=moderate
3=severe
4=very severe
5=plant dead

EXAMPLE 6

Field Trials

An emulsifiable concentrate of the present invention (Example 1. cyhexatin EC as previously described) was compared in field trials with a composition comprising 20% dicofol and 6.25% tetradifon (Childion) and a composition comprising 8% tetradifon (Tedion V-18) for controlling red spider mite (*Panonychus ulmi*) in apple orchards.

The apple orchards were sprayed with the various compositions following standard commercial practice. After periods of 10 and 30 days leaves from the sprayed trees were collected and the number of live red spider mites counted and then assessed in relation to the number of live red spider mites on the untreated controls. The final results were corrected for control mortality using the Henderson and Tilton formula and expressed as percentage kill. The results were expressed as percentage kill. The results were as follows:

| COMPOSITION | RATE APPLIED GRAMS/ HECTARE | KILL AFTER 10 DAYS | KILL AFTER 30 DAYS |
|---|---|---|---|
| TRIAL 1 | | | |
| Cyhexatin EC | 420 | 92.05 | 95.38 |
| Childion | 1180 | 58.48 | 84.57 |
| Tedion V-18 | 280 | 25.04 | 48.58 |
| TRIAL 2 | | | |
| Cyhexatin EC | 420 | 85.13 | 96.43 |
| Childion | 1180 | 75.08 | 82.30 |
| Tedion V-18 | 280 | 75.00 | 34.48 |
| TRIAL 3 | | | |
| Cyhexatin EC | 420 | 93.99 | 96.89 |
| Childion | 1180 | 43.84 | 88.92 |
| Tedion V-18 | 280 | 54.83 | 60.94 |

EXAMPLE 7

Phytotoxicity evaluation on apple

Cyhexatin e.c. (as produced in Example 1) applied at rates of between 300 and 600 g/ha to apple orchards did not induce significant russetting. This is commercially acceptable since russetting would be an indication of phytotoxicity.

EXAMPLE 8

Phytotoxicity evaluation of Fentin hydroxide e.c.

Tests have shown acceptable phytotoxicity ratings of the product produced by Example 3 when tested in comparison to commercial fentin hydroxide wettable powder formulations.

We claim:

1. A derivative of a biologically active triphenyl or tricyclohexyl substituted tin compound with a phosphate ester of an ethoxylated alkyl phenol or a lipophilic strong acid containing sulphur, or a salt thereof, wherein the lipophilic anion is an alkyl aryl sulphonate, a long chain optionally substituted alkyl sulphate, an ether sulphate or olefin sulphonate, or the corresponding acids of such lipophilic anions, alkyl in each instance containing from 6 to about 18 carbon atoms.

2. A derivative as claimed in claim 1 which is an alkyl benzene sulphonic acid derivative of a biologically active triphenyl or tricyclohexyl substituted tin compound.

3. A derivative as claimed in claim 2 which is an alkyl benzene sulphonic acid derivative of tricyclohexyltin.

4. A derivative as claimed in claim 2 which is an alkyl benzene sulphonic acid derivative of triphenyltin hydroxide.

5. A derivative as claimed in claim 3 which is a dodecyl benzene sulphonic acid derivative of tricyclohexyltin.

6. A derivative as claimed in claim 4 which is a dodecyl benzene sulphonic acid derivative of triphenyltin hydroxide.

7. A derivative as claimed in claim 3 which is a tridecyl benzene sulphonic acid derivative of tricyclohexyltin.

8. A derivative as claimed in claim 4 which is a tridecyl benzene sulphonic acid derivative of triphenyltin hydroxide.

9. An emulsifiable concentrate comprising a biologically active triphenyl or tricyclohexyl substituted tin compound, at least one mole equivalent thereof of an alkyl benzene sulphonic acid and an organic liquid.

10. An emulsifiable concentrate as claimed in claim 9 wherein the biologically active substituted tin compound is tricyclohexyltin or triphenyltin hydroxide.

11. A concentrate as claimed in claim 9 wherein the organic liquid is xylene; a propylbenzene fraction, a mixed napthalene fraction; dioctyl phthalate; kerosene; a polybutene; a mineral oil; a dimethyl amide of a fatty acid; an n-butyl ether of diethylene glycol; an ethyl ether of diethylene glycol; a methyl ether of diethylene glycol; a methyl ether of dipropylene glycol; an n-butyl ether of ethylene glycol; an ethyl, methyl or phenyl ether of ethylene glycol; a methyl ether of propylene or tripropylene glycol; or a mixture thereof.

12. An aqueous emulsion comprising an emulsifiable concentrate as claimed in claim 9 wherein the diluent is water.

13. A composition as claimed in claim 9 which contains, in addition, a surfactant.

14. A composition as claimed in claim 13 wherein the surfactant is an alkoxylation derivative of a fatty amine.

15. A method for controlling plant infestations which comprises applying a composition as claimed in claim 9 to the locus of the infestation.

16. A composition as claimed in claim 10 wherein the biologically active substituted tin compound is tricyclohexyltin for use in the control of animal and poultry ectoparasites.

17. An emulsifiable concentrate as claimed in claim 9 wherein the lipophilic anion is an alkyl aryl sulfonate.

* * * * *

UNITED STATES PATENT AND TRADEMARK OFFICE
CERTIFICATE OF CORRECTION

PATENT NO. : 4,581,373

DATED : April 8, 1986

INVENTOR(S) : Patrick J. Mulqueen and Robert Dutton

It is certified that error appears in the above-identified patent and that said Letters Patent is hereby corrected as shown below:

```
Col. 1, line 52, "concentration" should read --concentrated--
line 59, "liquids," should read --liquids.--
Col. 2, line 30, "or" should read --of--.
Col. 3, line 25, "of one" should read --one of--; line 58,
"surface" should read --surfactant--.
Col. 4, line 56, "cystallised" should read --crystallized--.
Col. 5, line 56, "asjusted" should read --adjusted--.
Col. 6, line 19, "does" should read --dose--.
```

Signed and Sealed this

Thirtieth Day of September 1986

[SEAL]

Attest:

DONALD J. QUIGG

Attesting Officer

Commissioner of Patents and Trademarks